United States Patent
Morrissey et al.

(10) Patent No.: US 9,289,703 B2
(45) Date of Patent: Mar. 22, 2016

(54) DISPOSABLE TANGENTIAL FLOW FILTRATION LINER WITH SENSOR MOUNT

(71) Applicant: EMD Millipore Corporation, Billerica, MA (US)

(72) Inventors: Martin Morrissey, Billerica, MA (US); Dennis Wong, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 408 days.

(21) Appl. No.: 13/868,372

(22) Filed: Apr. 23, 2013

(65) Prior Publication Data

US 2013/0233777 A1    Sep. 12, 2013

Related U.S. Application Data

(62) Division of application No. 12/784,094, filed on May 20, 2010, now Pat. No. 8,454,822.

(60) Provisional application No. 61/217,323, filed on May 29, 2009.

(51) Int. Cl.
*B01D 61/20* (2006.01)
*B01D 63/08* (2006.01)
(Continued)

(52) U.S. Cl.
CPC ............... *B01D 35/14* (2013.01); *B01D 61/20* (2013.01); *B01D 63/084* (2013.01); *G01L 7/082* (2013.01);
(Continued)

(58) Field of Classification Search
CPC ...... B01D 35/14; B01D 61/20; B01D 63/084; B01D 63/08; B01D 2313/04; B01D 2313/23; B01D 2313/44; B01D 2313/54; C02F 2103/343; C02F 2103/36; C02F 2313/04; C02F 2313/23; C02F 2313/44; C02F 2313/54; C02F 2209/03; G01N 1/10; G01N 1/18; G01N 1/22; G01N 1/28; G01N 1/34; G01N 1/40; G01N 1/4005; G01N 1/4011; G01N 1/4016; Y10T 436/25; Y10T 436/255; Y10T 436/25375; G01L 7/08; G01L 7/082; G01L 7/084; G01L 7/086; G01L 7/088; G01L 9/0041; G01L 2009/0066; G01L 2009/0067; G01L 2009/0069
USPC ............... 73/715–728, 863.23; 210/650, 739, 210/741, 767; 436/177, 178; 422/534, 535
See application file for complete search history.

(56) References Cited

U.S. PATENT DOCUMENTS 3,085,970 A    4/1963 Davis
3,520,803 A    7/1970 Iaconelli
(Continued)

FOREIGN PATENT DOCUMENTS

CN    2064262 U    10/1990
CN    1210476 A    3/1999
(Continued)

OTHER PUBLICATIONS

European Communications mailed Feb. 12, 2014 in corresponding European patent application No. EP 10164404.5.
(Continued)

*Primary Examiner* — Joseph Drodge
(74) *Attorney, Agent, or Firm* — Niels, Lemack & Frame, LLC

(57) ABSTRACT

Tangential flow filtration device is provided wherein liners are provided between the filtration element and the top and bottom holders or manifolds. The liners incorporate the flow channels and inlet and outlet ports, as well as a sensor mount. The liners are made of an inexpensive material and therefore are disposable after a single use, making it more cost effective to dispose of them than to clean the conventional manifolds. The sensor mount accommodates a removable sensor, and isolates it from the fluid path.

5 Claims, 3 Drawing Sheets

(51) Int. Cl.

| | |
|---|---|
| *G01L 7/08* | (2006.01) |
| *G01N 1/10* | (2006.01) |
| *G01N 1/40* | (2006.01) |
| *B01D 35/14* | (2006.01) |

(52) U.S. Cl.
CPC ............... *G01N 1/10* (2013.01); *G01N 1/4005* (2013.01); *B01D 2313/04* (2013.01); *B01D 2313/23* (2013.01); *B01D 2313/44* (2013.01); *B01D 2313/54* (2013.01); *C02F 2209/03* (2013.01); *Y10T 436/25* (2015.01); *Y10T 436/25375* (2015.01)

(56) References Cited

U.S. PATENT DOCUMENTS

| | | |
|---|---|---|
| 3,782,083 A | 1/1974 | Rosenberg |
| 4,113,627 A | 9/1978 | Leason |
| 4,261,834 A | 4/1981 | deWinter |
| 4,556,489 A | 12/1985 | Diettrich, Jr. et al. |
| 4,732,675 A | 3/1988 | Badolato et al. |
| 4,849,102 A | 7/1989 | Latour et al. |
| 4,867,876 A | 9/1989 | Kopf |
| 4,902,481 A | 2/1990 | Clark et al. |
| 5,034,124 A | 7/1991 | Kopf |
| 5,049,268 A | 9/1991 | Kopf |
| 5,096,582 A | 3/1992 | Lombardi et al. |
| 5,147,542 A | 9/1992 | Proulx |
| 5,176,828 A | 1/1993 | Proulx |
| 5,258,122 A | 11/1993 | Ha et al. |
| 5,342,517 A | 8/1994 | Kopf |
| 5,429,742 A | 7/1995 | Gutman et al. |
| 5,443,723 A | 8/1995 | Stankowski et al. |
| 5,445,737 A | 8/1995 | Ondrick |
| 5,599,447 A | 2/1997 | Pearl et al. |
| 5,693,892 A | 12/1997 | Batey |
| 5,855,778 A | 1/1999 | Hutchison et al. |
| 5,868,930 A | 2/1999 | Kopf |
| 6,406,623 B2 | 6/2002 | Petersen et al. |
| 6,736,980 B2 | 5/2004 | Moscaritolo |
| 6,790,599 B1 * | 9/2004 | Madou .......... 430/320 |
| 6,823,718 B2 | 11/2004 | Sandford et al. |
| 6,852,216 B2 | 2/2005 | Moscaritolo et al. |
| 7,094,346 B2 | 8/2006 | Osenar et al. |
| 7,137,390 B2 | 11/2006 | Fudge et al. |
| 7,306,727 B2 | 12/2007 | Perreault |
| 7,341,669 B2 * | 3/2008 | Ferguson ............ 210/741 |
| 7,473,404 B2 | 1/2009 | Chopard et al. |
| 7,771,380 B2 * | 8/2010 | Jonsson et al. ........... 604/5.01 |
| 8,177,974 B2 | 5/2012 | Hunt et al. |
| 8,454,822 B2 | 6/2013 | Morrissey et al. |
| 2003/0042182 A1 | 3/2003 | Moscaritolo |
| 2004/0226875 A1 | 11/2004 | Bartlett et al. |
| 2006/0060518 A1 | 3/2006 | Perreault |
| 2007/0023344 A1 | 2/2007 | Kemp |
| 2007/0023348 A1 | 2/2007 | Harms et al. |
| 2007/0138082 A1 | 6/2007 | Connors, Jr. et al. |
| 2007/0241048 A1 | 10/2007 | Hunt et al. |
| 2008/0257813 A1 | 10/2008 | Proulx et al. |
| 2009/0060789 A1 | 3/2009 | Aas et al. |
| 2010/0237013 A1 | 9/2010 | Burke et al. |
| 2011/0127203 A1 | 6/2011 | Morrissey et al. |
| 2011/0174711 A1 | 7/2011 | Morrissey et al. |
| 2012/0192958 A1 | 8/2012 | Hunt et al. |

FOREIGN PATENT DOCUMENTS

| | | |
|---|---|---|
| CN | 101134157 A | 3/2008 |
| DE | 4338063 A1 | 5/1995 |
| EP | 0233339 A1 | 8/1987 |
| EP | 0345209 A2 | 12/1989 |
| EP | 1415698 A1 | 5/2004 |
| EP | 1637213 A1 | 3/2006 |
| EP | 1844846 A2 | 10/2007 |
| EP | 2106842 B1 | 9/2013 |
| GB | 358526 | 10/1931 |
| JP | 53-103983 A | 9/1978 |
| JP | 55-5684 A | 1/1980 |
| JP | 8-89766 A | 4/1996 |
| JP | 2000-510722 A | 8/2000 |
| JP | 2003-502140 A | 1/2003 |
| JP | 2006-88152 A | 4/2006 |
| JP | 2008-238167 A | 10/2008 |
| WO | 97/28889 A1 | 8/1997 |
| WO | 97/42410 A1 | 11/1997 |
| WO | 00/78429 A2 | 12/2000 |
| WO | 02/085511 A1 | 10/2002 |
| WO | 2008/107652 A1 | 9/2008 |

OTHER PUBLICATIONS

Final Rejection mailed Feb. 28, 2014 in co-pending U.S. Appl. No. 13/446,103.
Notice of Allowance mailed Apr. 30, 2015 in co-pending U.S. Appl. No. 13/446,103.
Office Action mailed May 5, 2015 in co-pending U.S. Appl. No. 12/844,282.
Office Action mailed May 16, 2014 in co-pending U.S. Appl. No. 12/844,282.
Pall BioPharmaceuticals, Selection Guide System Data Sheet BP-1070, "Centrasette-tm-P: Economical sanitary systems for small production and benchtop use", as early as 2004, 1 page.
BioProcess International, Supplement, Apr. 2004, p. 33, "Manufacturing Conjugate Vaccines", Sellick.
European Communication dated Jan. 12, 2006 in co-pending European patent application No. EP 05255614.9.
European Search Report dated Aug. 26, 2008 in co-pending European patent application No. EP 07251587.
European Search Report dated Aug. 19, 2009 in co-pending European patent application No. EP 09166040.
European Communication dated Aug. 26, 2009 in co-pending patent application No. EP 07251587.
English translation of Chinese Communication dated Oct. 30, 2009 in co-pending Chinese patent application No. CN 200710128282.3.
English translation of Chinese Communication dated Jun. 2, 2010 in co-pending Chinese patent application No. CN 200710128282.3.
Japanese Communication, with English translation, dispatched Oct. 21, 2008 in co-pending Japanese patent application No. JP 2007-103871.
Japanese Communication, with English translation, dispatched May 11, 2010 in co-pending Japanese patent application No. JP 2007-103871.
Chinese Communication issued Sep. 24, 2012 in corresponding Chinese patent application No. CN 201010197766.5.
European Communication dated Oct. 7, 2010 in corresponding European patent application No. EP 10164404.5.
Japanese Communication, with English translation, mailed Sep. 13, 2011 in corresponding Japanese patent application No. JP 2010-124907.
Chinese Communication mailed Nov. 5, 2012 in co-pending Chinese patent application No. 201010281130.9.
European Communication dated Dec. 20, 2010 in co-pending European patent application No. EP 10171374.1.
Japanese Communication, with English translation, dispatched Oct. 25, 2011 in co-pending Japanese patent application No. JP 2010-175454.
Extended European Search Report received for co-pending EP Patent Application No. 08153282.2, mailed on Jul. 20, 2009, 5 pages.
Office Action mailed Aug. 7, 2012 in co-pending U.S. Appl. No. 13/446,103.
Final Rejection mailed Jan. 14, 2013 in co-pending U.S. Appl. No. 13/446,103.
Office Action mailed Mar. 25, 2010 in co-pending U.S. Appl. No. 12/075,210.
Final Rejection mailed Nov. 26, 2010 in co-pending U.S. Appl. No. 12/075,210.
Office Action mailed Sep. 5, 2012 in co-pending U.S. Appl. No. 12/844,282.

(56) References Cited

OTHER PUBLICATIONS

Final Rejection mailed Mar. 7, 2013 in co-pending U.S. Appl. No. 12/844,282.
Office Action mailed Jul. 18, 2014 in co-pending U.S. Appl. No. 12/075,210.
Notice of Opposition and Letter Regarding the Opposition Procedure (with English translation) mailed Jun. 23, 2014 in European patent No. EP 2106842 B1, 48 pages.
DuPont Engineering Polymers, E. I. du Pont de Nemours and Company, 2000, Design Guide—Module 1, Excerpt from General Design Principles for DuPont Engineering Polymers, pp. 26-27, 4 pages, downloadable in full on the Internet from the following link: http://www2.dupont.com/Plastics/en_US/assets/downloads/design/H76838.pdf (D2 in Opposition/Letter to EP 2106842 B1).
Allied Signal Plastics, 1996 AlliedSignal, Inc., Excerpt from Empfehlungen fur den Konstrukteur (Recommendations for the Designer), pp. III-15 through III-18, 9 pages, downloadable in full on the Internet from the following link: http://ww3.cad.de/foren/ubb/uploads/Tricksucher/09-96-BG3049-500.pdf (D3 in Opposition/Letter to EP 2106842 B1).
Sartorius-Werke GmbH, Gerate-Ubersicht, SM 165 00, 4 pages, apparatus catalog showing product offerings during the 1970's and 1980's (as attested to in the affidavits of Ulrich Grummert and Gustav-Helge Schramme and shown on the list for some of the products) particularly for Sales order No. SM 165 25, relating to filtration apparatus (V1 in Opposition/Letter to EP 2106842 B1).
Sartorius-Werke GmbH, Gerate-Ubersicht, SM 168 00, 5 pages, apparatus catalog showing product offerings during the 1970's and 1980's (as attested to in the affidavits of Ulrich Grummert and Gustav-Helge Schramme and shown on the list for some of the products) particularly for Sales order Nos. SMK 168 96, relating to filtration pump/base, and SM 165 25, relating to filtration apparatus (V2 in Opposition/Letter to EP 2106842 B1).
Sartorius-Werke GmbH, Apparatur mit der Filtrationsvorrichtung and dem Unterteil (Entire apparatus with the filtration apparatus and the base), 2 page design drawings re: No. 80 185.000-00, produced between Nov. 3, 1969 and Oct. 26, 1971 (V3 in Opposition/Letter to EP 2106842 B1).
Sartorius-Werke GmbH, Stuckliste zur Filtrationsvorrichtung (Parts List for the filtration apparatus), re: No. 80 185.200-00, 1 page, produced between Jan. 30, 1970 and May 22, 1985 (V4 in Opposition/Letter to EP 2106842 B1).
Sartorius-Werke GmbH, Konstruktionszeichnung (Design Drawings), re: No. 80 185.200-02 Platte, 1 page, 1970, (V5 in Opposition/Letter to EP 2106842 B1).
Sartorius-Werke GmbH, Konstruktionszeichnung (Design Drawings), re: No. 80 185.200-03 Platte, 1 page, 1970, (V6 in Opposition/Letter to EP 2106842 B1).
Sartorius-Werke GmbH, Konstruktionszeichnung der Platte (Design Drawings of the Plate), re: No. 80 185.200-01 Platte, 2 pages, produced between Jan. 10, 1970 and Apr. 26, 1972, (V7 in Opposition/Letter to EP 2106842 B1).
Sartorius Membranfilter GmbH, Aufbau der Filtrationsvorrichtung (Construction of the Filtration Apparatus), SM 165 25, 3 pages, available during the 1970's and 1980's (as attested to in the affidavits of Ulrich Grummert and Gustav-Helge Schramme) (V8 in Opposition/Letter to EP 2106842 B1).
Sartorius GmbH, Auszug aus dem Verkaufskatalog "Laborfiltration, Mikrobiologie, Elektrophorese" (Excerpts from the Sales Catalog "Laboratory Filtration, Microbiology, Electrophoresis", distributed prior to 1993 (as attested on p. 12 of the English translation of the Opposition Letter), 10 pages (V9 in Opposition/Letter to EP 2106842 B1).
Sartorius GmbH, Auszug Preisliste "Filtrationstechnik, Laborfiltration, Mikrobiologie, Elektrophorese" (Excerpts from Price List for Filtration Technology, Laboratory Filtration, Microbiology, Electrophoresis), Apr. 15, 1985, 5 pages (V10 in Opposition/Letter to EP 2106842 B1).
Fachzeitschrift "Die Pharmazeutische Industrie" (The technical journal, "The Pharmaceutical Industry"), Symposium "Membranfiltration heute" (Membrane Filtration Today), vol. 38, Issue 2a, 1976, p. 113-115, 4 pages, "Untersuchungen zur Sterilfiltration einiger Plasmaproteinpraparate mit Hilfe der tangentialen Uberstromung" ("Investigations for the Sterile Filtration of Some Plasma Protein Preparations by Use of Tangential Flow)", by Von D. Stampe, (V11 in Opposition/Letter to EP 2106842 B1).
Eidesstattliche Versicherung (Affidavit) of Ulrich Grummert, 2 pages, May 26, 2014, submitted in support of Opposition/Letter to EP 2106842 B1.
Eidesstattliche Versicherung (Affidavit) of Gustav-Helge Schramme, 2 pages, May 30, 2014, submitted in support of Opposition/Letter to EP 2106842 B1.
Office Action mailed Dec. 17, 2014 in co-pending U.S. Appl. No. 13/446,103.
Final Rejection mailed Nov. 21, 2014 in co-pending U.S. Appl. No. 12/844,282.
Examiner's Answer to Reply Brief mailed Sep. 24, 2013 in co-pending U.S. Appl. No. 13/446,103.

\* cited by examiner

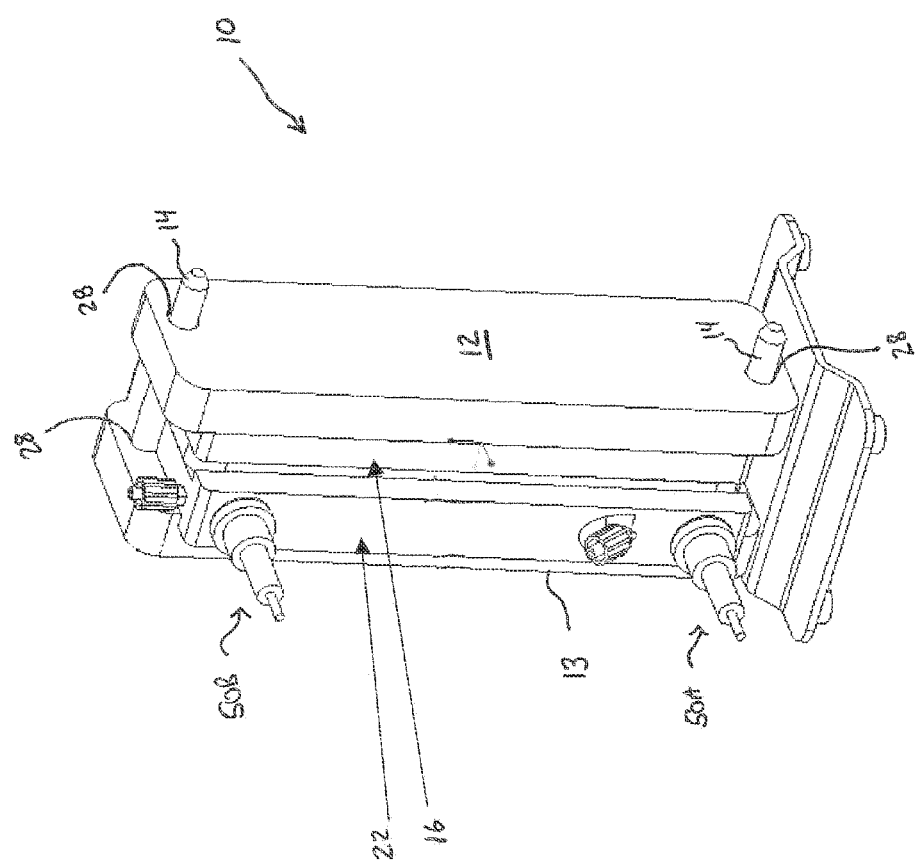

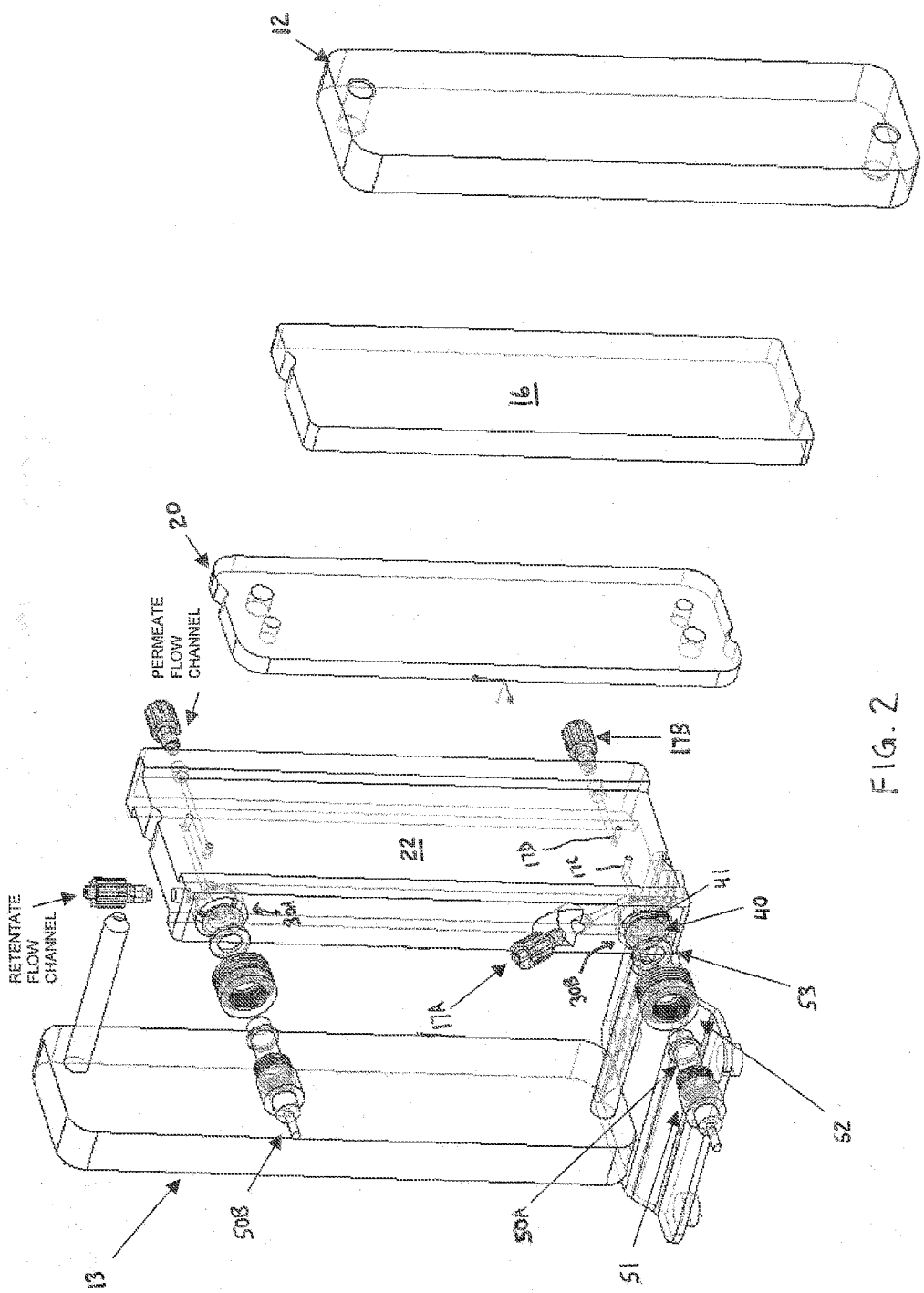

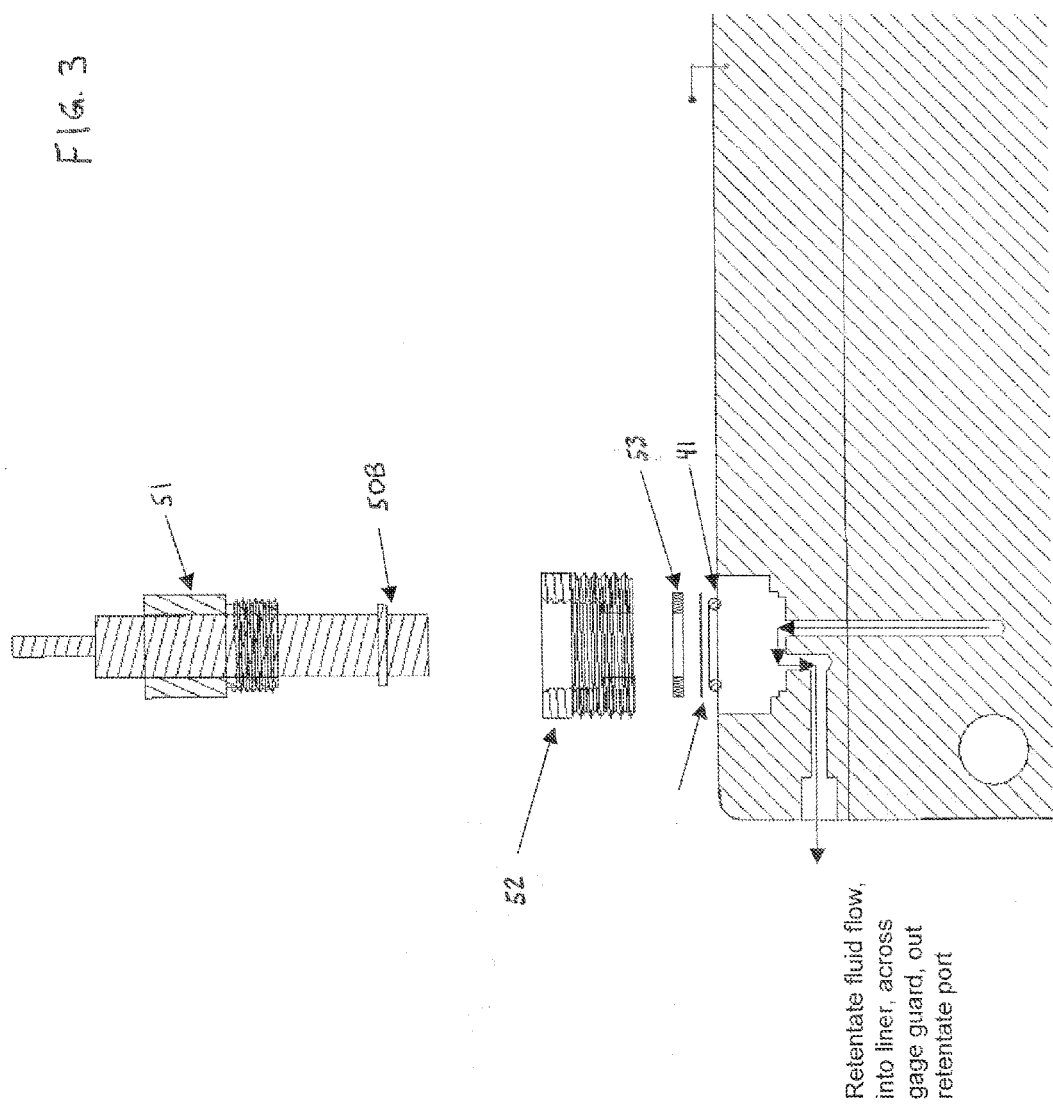

DISPOSABLE TANGENTIAL FLOW FILTRATION LINER WITH SENSOR MOUNT

This application is a divisional of U.S. patent application Ser. No. 12/784,094 filed May 20, 2010, which claims priority of U.S. Provisional Application Ser. No. 61/217,323 filed May 29, 2009, the disclosures of which are incorporated herein by reference.

BACKGROUND OF THE INVENTION

Tangential Flow Filtration (TFF) is a separation process that uses membranes to separate components in a liquid solution or suspension on the basis of size or molecule weight differences. Applications include concentration, clarification, and desalting of proteins and other biomolecules such as nucleotides, antigens, and monoclonal antibodies; buffer exchange; process development; membrane selection studies; pre-chromatographic clarification to remove colloidal particles; depyrogenation of small molecules such as dextrose and antibiotics; harvesting, washing or clarification of cell cultures, lysates, colloidal suspensions and viral cultures; and sample preparation.

In TFF, the solution or suspension to be filtered is passed across the surface of the membrane in a cross-flow mode. The driving force for filtration is the transmembrane pressure, usually created with a peristaltic pump in disposable TFF applications. The velocity at which the filtrate is passed across the membrane surface also controls the filtration rate and helps prevent clogging of the membrane. Because TFF recirculates retentate across the membrane surface, membrane fouling is minimized, a high filtration rate is maintained, and product recovery is enhanced.

Conventional TFF devices are formed of a plurality of elements, including a pump, a feed solution reservoir, a filtration module and conduits for connecting these elements. In use, the feed solution is directed from the feed solution reservoir to the filtration module while the retentate from the filtration module is recirculated from the filtration module to the feed solution reservoir until the desired volume of retentate is obtained. The membrane is sandwiched between top and bottom manifolds or holders, which serve to provide accurate mechanical constraint against the internal hydraulic pressure of the device, and also serve to distribute the filtration stream across the multiple flow paths within the device. These manifolds or holders are typically made of stainless steel and must be cleaned and validated prior to each use, particularly in biopharmaceutical and other sanitary applications. This is an expensive and time-consuming process.

Where cleaning and validation steps are desired to be eliminated when replacing the filtration medium, disposable liners can be used instead of the reusable stainless steel liners. The liners incorporate the flow channels and inlet and outlet ports that were previously present in the manifolds, and isolate the process fluid from coming into contact with the TFF holder. The liners can be made of an inexpensive material and therefore are disposable after a single use, making it more cost effective to dispose of them than to clean the conventional manifolds. In addition, the liners can be pre-sterilized. In order to provide sufficient strength and rigidity under operating conditions, the liners can have a grid pattern of ribs that abut the holder plates to help prevent the liners from torquing under clamping force.

It also would be desirable to incorporate sensors in the liners, for measuring various process parameters, such as pressure, without having to clean or sterilize the sensors when replacing the filtration medium and/or liners.

SUMMARY OF THE INVENTION

The shortcomings of the prior art are overcome by the embodiments disclosed herein, which include a tangential filtration assembly including one or more preferably disposable liners having one or more sensors disposed therein. The sensor(s) are isolated from the fluid and are removable from the liner. As a result, after use the liner can be disposed and the sensor(s) reused without having to clean the sensor.

In accordance with certain embodiments, a tangential flow filtration device is provided wherein one or more liners are located between the filtration element and the top and bottom holders or manifolds. The liners incorporate the flow channels and inlet and outlet ports that are conventionally present in the stainless steel manifolds. The liners are made of an inexpensive material and therefore are disposable after a single use, making it more cost effective to dispose of them than to clean the conventional manifolds. In addition, the liners can be pre-sterilized. In order to provide sufficient strength and rigidity under operating conditions, the liners can have a grid pattern of ribs that abut the holder plates to help prevent the liners from torquing under clamping force.

The one or more liners includes one or more sensor ports or mounts, for removably affixing a sensor to the liner. A diaphragm is disposed between the sensor and the fluid passageway in the liner, isolating the sensor components from directly contacting fluid in the passageway. The sensor remains capable of sensing the pressure of the fluid in the passageway, but the presence of the diaphragm prevents the sensor from being contaminated by the fluid.

BRIEF DESCRIPTION OF THE DRAWINGS

FIG. 1 is perspective view of a tangential flow filtration assembly in accordance with certain embodiments;

FIG. 2 is an exploded view of the assembly of FIG. 1; and

FIG. 3 is an exploded view showing a sensor and a sensor port in accordance with certain embodiments.

DETAILED DESCRIPTION OF THE INVENTION

Turning first to FIG. 1, there is shown a filtration device in accordance with certain embodiments. The device 10 includes a top holder plate 12 and a spaced bottom holder plate 13. The holder plates 12, 13 are preferably made of stainless steel and are sufficiently rigid and durable to provide accurate and effective mechanical constraint of the assembly against internal hydraulic operating pressures, such as 50-60 psi. Apertures 28 are provided in the holder plates 12, 13 and in each layer of the assembly to accommodate tie rods or threaded pins or bolts 14 or other clamping device to secure the assembly together. Spacers (not shown) can be provided, and can be spring-loaded. No filtration stream passageways are present in the holder plates 12, 13.

Positioned beneath holder plate 12 in the assembled state is disposable liner 16. The liner 16 is preferably made of inexpensive material, suitable for the application, that is acceptable for the particular assay, such as pharmaceutical assays, (and preferably is government approved). Suitable materials of construction include plastics, such as polystyrene, preferably polyolefins, such as polypropylene, polyethylene, copolymers and mixtures thereof. Polysulfone is particularly preferred in view of its strength and rigidity. The liner 16 is preferably molded with passageways and openings. Alternatively, and less preferred, it may be formed by milling, drilling and other such methods.

A filtration element 20 is sandwiched between liner 16 and a second disposable liner 22. The filtration element 20 can be a single membrane, and is preferably a plurality of stacked membranes, such as stacked ultrafiltration or microfiltration membranes, most preferably provided in the form of a cassette. Although a single cassette of membranes is shown, those skilled in the art will appreciate that multiple cassettes can be used. Suitable cassettes are sold under the name PELLICON® and are commercially available from Millipore Corporation.

As is conventional in the art, the liner 22 includes a first port 17A, one or more sub-ports 17C, a second port 17B and one or more sub-ports 17D (FIG. 2). Port 17A is for introduction of feed or removal of retentate, depending on its orientation within the assembly, with port 17B for removal of permeate, while preventing admixture of the filtrate with the retentate or feed, as is conventional. Port 17A is in fluid communication with the one or more sub-ports 17C. Port 17A is in fluid communication with 17C and with the sensor port closest to it. Port 17A also is in fluid communication with the feed port of the cassette, e.g., a PELLICON® cassette. Port 17B is in fluid communication with the one or more sub-ports 17D. Port 17B is only in communication with 17D and the permeate drain port of the cassette. The ports 17A and 17B may be located on opposite sides of the liner in order to provide adequate spacing and avoid interferences with other components. However, where spacing is sufficient or no interference occurs, they may be located on the same side. Each port 17A, 17B is in fluid communication with flow paths or passageways in the liner body that communicate with respective apertures to accommodate flow of feed, retentate or permeate as is conventional, thereby defining multiple flow paths for the filtration stream within the device.

The passageways can be tapered, narrowing as they proceed away from their respective port, to normalize pressure at each of the sub-ports 17C and 17D.

In certain embodiments, one side of one or both of the liners 16, 22 can include a plurality of inter-engaging ribs. The ribs provide added rigidity to the liners, and can be formed in the molding process. The ribs, when present, are positioned on the side of the liner that contacts the holder plate 12 or 13. The ribs extend from one side of the liner to the other, except where interrupted by a port. When assembled, there is significant clamping force applied to the filter element 20 and the liner, with sealing taking place between the smooth side of the liner 16, 22 and the filter element 20. The ribs assist in effectively assemble the liners in the filtration device of the invention, in sealing engagement upon the application of pressure, without the necessity of having corresponding grooves in the holder plates to mate with the ribs. Accordingly, the respective surfaces of the holder plates that abut the grids of the liners can be flat, and need not be specially designed to fit the liners.

In certain embodiments, one or more sensors, preferably two sensors such as feed pressure sensor 50A and retentate pressure sensor 50B, are removably connected to mount ports in one or more of the disposable liners. For purposes of illustration, two ports 30A, 30B are shown in liner 22. The port or ports 30A, 30B are each positioned to communication with a fluid path, so that a characteristic of the fluid in the fluid path (e.g., pressure) can be measured. A membrane or diaphragm 40, such as a diaphragm made of PVDF or polyolefin, preferably polyethylene, for example, is positioned over the port 30A (or 30B) in order to isolate, during operation, fluid in the fluid path from the sensor components. An O-ring 41 or the like can be used to seal the diaphragm 40 to the port. The membrane or diaphragm can be permanently attached to the port if desired.

In certain embodiments, the sensors are attached to the liner 22 using a diaphragm compression nut 52, as best seen in FIGS. 2 and 3. The nut 52 is internally threaded, the internal threads corresponding to external threads on a sensor compression nut 51 positioned on the sensor 50A so that the sensor 50A may be screwed into the nut 52. The sensor compression nut 51 compresses the sensor flange into the larger diaphragm compression nut 52. The nut 52 is also externally threaded, the external threads corresponding to threads in the port 30B so that the nut 52 may be screwed into the port. A slip washer 53 can be positioned between the compression nut 52 and the diaphragm as shown. The nut 52 compresses the O-ring 41, diaphragm 40 and washer 53 in place. Those skilled in the art will appreciate that other means of attaching the sensor to the mount port can be used, such as a press fit into the port or a suitable receptacle affixed to the port, clamps or fasteners that hold the sensor in place, etc.

In the assembled condition, the operative portion of the sensor is positioned directly against the membrane or diaphragm. The membrane or diaphragm is made of a sufficiently flexible material so that it deflects in response to pressure, remains continuous and does not break or lose the ability to isolate the sensor from the fluid path. The membrane or diaphragm can be semi-permeable or non-permeable. It is preferably of sterilizing grade.

The presence of two sensors 50A, 50B, one measuring feed pressure and the other retentate pressure, allows the transmembrane pressure to be calculated, as transmembrane pressure is the average of the feed and retentate pressures less the filtrate pressure. The filtrate pressure can be determined in a conventional manner well known to those skilled in the art. In use, the removable sensors are preferably in electrical communication with a control unit, which can record the relevant process parameters, such as feed pressure, retentate pressure, transmembrane pressure, etc., and can control the parameters accordingly.

By removably connecting the sensors to the mount ports on the disposable liner(s) in accordance with the embodiments disclosed herein, the sensors remain isolated from the fluid paths and can be readily removed from the liners and reused, while the liners can be discarded after use. This results in quick and easy system set up.

The length of the ports 30A and B are such that preferably there is little or no deadleg between the diaphragm of the sensor port and the conduit in which the fluid to be sensed passes. This ensures that no fluid is lost or becomes stagnant.

Suitable sensors include electromechanical sensors, due to cost, accuracy, reliability and availability concerns. Electromechanical sensors include a strain gauge bonded to a thin metal diaphragm. Deformation of the diaphragm results in deformation of the strain gauge, sending a proportional electrical signal to the control unit. Those skilled in the art will appreciate that sensors that operate using different technologies also could be used.

What is claimed is:

1. A method of filtering a sample, comprising:
   providing a top plate, a bottom plate spaced from said top plate, a filtration member positioned between said top plate and said bottom plate, and at least one disposable liner positioned between said top plate and said filtration member, said liner having a fluid inlet, a fluid outlet, at least one fluid path within said liner, and a sensor port in fluid communication with said fluid path;

sealing a diaphragm to said sensor port;

attaching a sensor to said sensor port such that said diaphragm isolates said sensor from direct contact with fluid in said fluid path when fluid is in said fluid path;

introducing a fluid sample to be filtered into said filtration apparatus; and sensing pressure in said at least one fluid path with said sensor through said diaphragm.

2. The method of claim 1, further comprising providing at least a second fluid path, a second sensor port, and a second diaphragm sealed to said second sensor port in said liner, and removably connecting a second sensor to said second sensor port for sensing pressure in said second fluid path through said second diaphragm without contacting fluid in said second fluid path.

3. The method of claim 1, further comprising removing said sensor from said sensor port, said sensor being free from contamination by said fluid not requiring cleaning.

4. The method of claim 1, wherein said diaphragm comprises PVDF or polyethylene.

5. The method of claim 1, wherein said diaphragm is semipermeable.

* * * * *